(12) United States Patent
Berg et al.

(10) Patent No.: US 7,252,681 B2
(45) Date of Patent: Aug. 7, 2007

(54) HEART VALVE STRUCTURES

(75) Inventors: Todd A Berg, Stillwater, MN (US);
Alex A Peterson, Maple Grove, MN (US); Matthew W Weston, Little Canada, MN (US)

(73) Assignee: St. Medical, Inc., St. Paul, MN (US)

( * ) Notice: Subject to any disclaimer, the term of this patent is extended or adjusted under 35 U.S.C. 154(b) by 0 days.

(21) Appl. No.: 10/368,085

(22) Filed: Feb. 13, 2003

(65) Prior Publication Data

US 2003/0171805 A1    Sep. 11, 2003

Related U.S. Application Data

(60) Provisional application No. 60/357,166, filed on Feb. 14, 2002.

(51) Int. Cl.
*A61F 2/24* (2006.01)

(52) U.S. Cl. .................. 623/2.14; 623/2.18

(58) Field of Classification Search ........ 623/2.1–2.19, 623/2.38
See application file for complete search history.

(56) References Cited

U.S. PATENT DOCUMENTS

| | | | | |
|---|---|---|---|---|
| 4,106,129 A | 8/1978 | Carpentier et al. | ............ | 3/1.5 |
| 4,343,048 A | 8/1982 | Ross et al. | ............ | 3/1.5 |
| 4,501,030 A | 2/1985 | Lane | ............ | 3/1.5 |
| 4,851,000 A | 7/1989 | Gupta | ............ | 623/2 |
| 5,037,434 A | 8/1991 | Lane | ............ | 623/2 |
| 5,156,621 A | 10/1992 | Navia et al. | ............ | 623/2 |
| 5,352,240 A | 10/1994 | Ross | ............ | 623/2 |
| 5,489,297 A | 2/1996 | Duran | ............ | 623/2 |
| 5,545,215 A | 8/1996 | Duran | ............ | 623/2 |
| 5,549,665 A * | 8/1996 | Vesely et al. | ............ | 623/2.14 |
| 5,562,729 A | 10/1996 | Purdy et al. | ............ | 623/2 |
| 5,824,065 A | 10/1998 | Gross | ............ | 623/2 |
| 5,855,601 A * | 1/1999 | Bessler et al. | ............ | 623/2.38 |
| 5,855,602 A | 1/1999 | Angell | ............ | 623/2 |
| 5,876,445 A * | 3/1999 | Andersen et al. | ............ | 623/23.7 |
| 6,296,662 B1 | 10/2001 | Caffey | ............ | 623/2.18 |
| 6,309,417 B1 | 10/2001 | Spence et al. | ............ | 623/2.11 |
| 6,350,282 B1 * | 2/2002 | Eberhardt | ............ | 623/2.13 |
| 6,461,382 B1 * | 10/2002 | Cao | ............ | 623/2.19 |
| 6,558,418 B2 * | 5/2003 | Carpentier et al. | ............ | 623/2.14 |
| 6,589,279 B1 * | 7/2003 | Anderson et al. | ............ | 623/2.13 |
| 6,610,088 B1 * | 8/2003 | Gabbay | ............ | 623/2.38 |

(Continued)

FOREIGN PATENT DOCUMENTS

CA    1228203 A    10/1987

(Continued)

Primary Examiner—William H Matthews
(74) Attorney, Agent, or Firm—Fish & Neave IP Group Ropes & Gray LLP; Paul Leblond

(57) ABSTRACT

A replacement heart valve structure including a structure of tissue which is an intact, mammalian heart valve that has been harvested and treated to preserve it. A conventional fabric sleeve is typically disposed concentrically around the outside of the tissue structure. A support structure is included to facilitate implanting the heart valve by somewhat increasing the stability of the heart valve structure, but without unduly rigidifying it. An annular sewing cuff may be added adjacent the blood inflow end of the valve structure to facilitate making the annular suture line that is required at that end.

18 Claims, 6 Drawing Sheets

U.S. PATENT DOCUMENTS

| | | | |
|---|---|---|---|
| 6,635,085 B1 * | 10/2003 | Caffey et al. | 623/2.1 |
| 2002/0032481 A1 * | 3/2002 | Gabbay | 623/2.11 |
| 2002/0035860 A1 | 3/2002 | Lam | 72/298 |
| 2002/0055775 A1 | 5/2002 | Carpentier et al. | 623/2.17 |
| 2002/0173842 A1 * | 11/2002 | Buchanan | 623/2.14 |
| 2003/0149477 A1 * | 8/2003 | Gabbay | 623/2.14 |

FOREIGN PATENT DOCUMENTS

| | | |
|---|---|---|
| WO | WO 00/42950 A | 7/2000 |
| WO | WO 01/49217 A | 7/2001 |

* cited by examiner

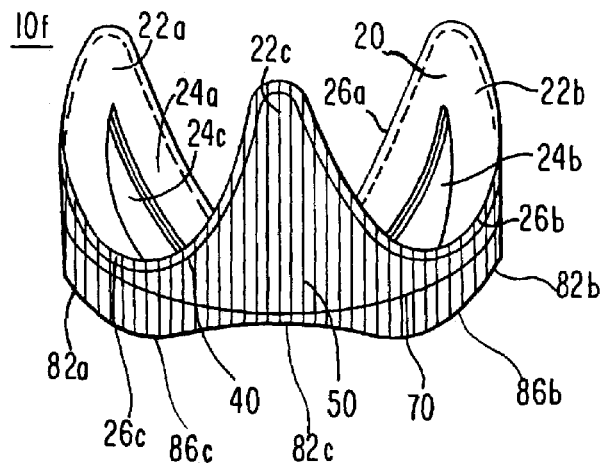
FIG. 19
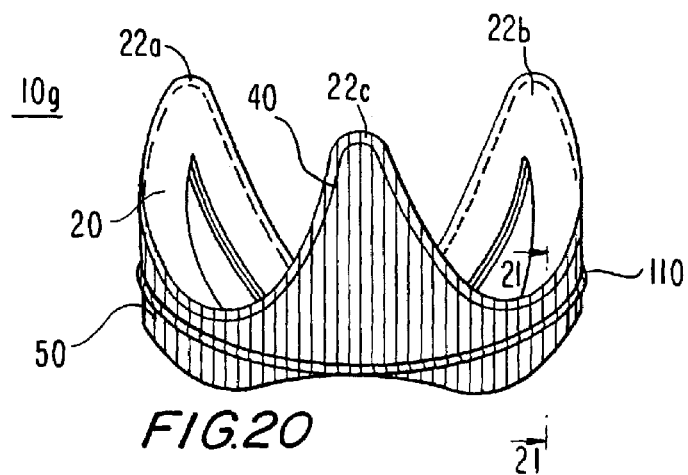
FIG. 20
FIG. 21
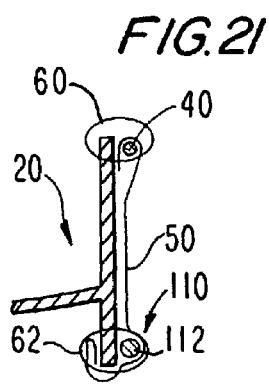
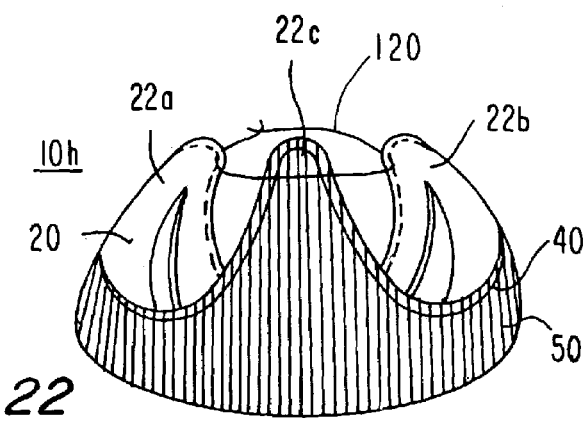
FIG. 22

HEART VALVE STRUCTURES

This application claims the benefit of U.S. provisional patent application 60/357,166, filed Feb. 14, 2002, which is hereby incorporated by reference herein in its entirety.

BACKGROUND OF THE INVENTION

One of the known techniques for replacing a heart valve in a human patient is to use a valve harvested from another mammal. Although the invention will be described for the most part with reference to replacing a patient's aortic valve (i.e., the valve between the left ventricle and the aorta), the principles of the invention can be adapted to other heart valve replacement procedures. Similarly, although heart valves harvested from pigs (porcine heart valves) are generally used, valves harvested from other mammals are possible alternatives.

In a known technique, a heart valve is harvested intact from a pig and treated to preserve it. (All references herein to such heart valves will be understood to include the immediately adjacent tissue, so that the structure thus referred to is an intact tube of tissue with the valve leaflets inside.) A so-called "stentless valve" is constructed by stitching a sleeve of fabric substantially concentrically around the outside of the harvested and preserved valve tissue. The resulting composite structure is sutured into the patient at the location from which the patient's natural valve leaflets have been removed. Two annular suture lines are typically employed. (Terms like "annular" and "annulus" are used herein solely as geometrical terms, and not to refer to any anatomical location or structure.) One suture line is located annularly around the valve adjacent the blood inflow ("proximal") end. The other suture line is located annularly around the valve adjacent the blood outflow ("distal") end. These two suture lines are generally regarded as necessary to ensure that there is no leakage of blood around the valve. The outflow suture line is also generally regarded as necessary to pin the commissure posts of the valve back (i.e., radially outward) against the root of the patient's aorta. The commissure posts of the valve are typically relatively long and flexible, and if they are not pinned back, they can fold over onto the valve leaflets in an undesirable way (e.g., impacting the leaflets and causing unnecessary wear). Over time (after implantation) the patient's natural body tissue is believed to advantageously grow into the fabric sleeve around the other material of the valve (i.e., the harvested and preserved valve tissue).

The high degree of flexibility of stentless valves of the type described above is believed to be beneficial to the patient. Such valves may compare favorably to the more rigid valves known as "stented" valves in respects such as the following: The rigidity of stented valves may stress the leaflets in the valve, which can cause tearing or calcification of the leaflets, which in turn can shorten the life of a stented valve. However, the stentless valves described above are thought by some to be somewhat more difficult to implant than stented valves or mechanical valves. As has been mentioned, stentless valves typically require two annular suture lines, whereas stented valves typically require only one annular suture line near the proximal end (because of the considerable stiffness imparted to the valve by the stent (typically metal) that forms part of the valve structure). Also, the high degree of flexibility of stentless valves can allow the commissure posts of the valve to fold down in the surgeon's way during placement of the first (inflow) suture line, and/or to permit one or more of those posts to be slightly mislocated when the final (outflow) suture line is made, with the possible result that the finally implanted valve may not close as completely and perfectly as it otherwise would.

In view of the foregoing, it is an object of this invention to improve heart valves of the stentless type described above.

It is another object of the invention to provide stentless heart valves that are more easily and more reliably implanted.

SUMMARY OF THE INVENTION

These and other objects of the invention are accomplished in accordance with the principles of the invention by providing heart valves that include a harvested and preserved mammalian heart valve and a structure for flexibly and resiliently supporting at least the commissure posts of the heart valve. A fabric sleeve may be provided around the other components of the valve structure. The support structure preferably follows at least portions of the blood outflow edge of the valve, and the portions of the support structure that thus follow the blood outflow edge are preferably at least partly secured to the other components of the valve by the same stitching that connects the blood outflow edges of the tissue structure and the fabric sleeve. In addition to the commissure post support, the heart valve may also be provided with flexible and resilient annular support structures adjacent the inflow end. As an alternative or addition to the inflow end support, the heart valve may be provided with an annular sewing cuff adjacent the inflow end.

The support structure or structures provided in heart valves in accordance with this invention are preferably much more flexible than the stents typically provided in stented heart valves. For example, the supports provided in accordance with this invention may be characterized as providing "minimal" support. This amount of support may be described as sufficient to keep various parts of the tissue structure in their natural (native) relative positions during implantation of the valve in a patient and in the absence of significant external distorting force. However, the amount of support provided is preferably not significantly greater than the minimum amount required to accomplish the objectives described in the preceding sentence. The valves of this invention therefore have a very high degree of flexibility, which may be slightly less than the flexibility of a completely unsupported valve, but much greater than the flexibility of typical stented or mechanical valves.

Further features of the invention, its nature and various advantages will be more apparent from the accompanying drawings and the following detailed description of the preferred embodiments.

BRIEF DESCRIPTION OF THE DRAWINGS

FIG. 19 is a view similar to FIG. 1 showing yet another illustrative embodiment of the invention.

FIG. 20 is another view similar to FIG. 1 for still another illustrative embodiment of the invention.

FIG. 21 is a simplified sectional view taken along the line 21-21 in FIG. 20.

FIG. 22 is another view similar to FIG. 1 for yet another illustrative embodiment of the invention.

DETAILED DESCRIPTION OF THE
PREFERRED EMBODIMENTS

Figure 1:
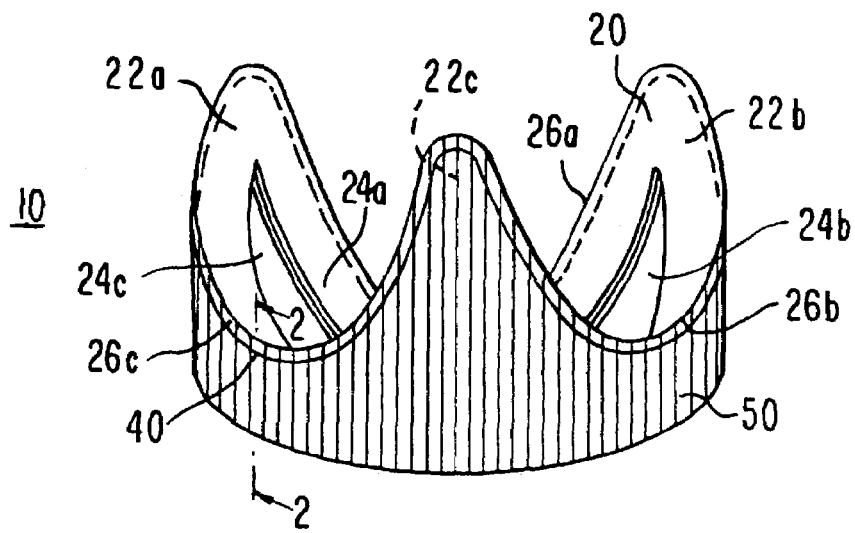
FIG. 1 is a simplified elevational view of an illustrative embodiment of a heart valve structure in accordance with the invention.

In the illustrative replacement heart valve structure 10 shown in FIG. 1, component 20 is a harvested and preserved, intact, porcine heart valve. The porcine heart valve is an annular tissue structure and includes three commissure posts 22a, 22b, and 22c, and three valve leaflets 24a, 24b, and 24c. This tissue structure has been harvested and preserved in a conventional manner. In the illustrative embodiment shown in FIG. 1, the bottom (blood inflow) edge of the tissue is a relatively straight annulus. In other embodiments the inflow edge may be scalloped. (Such scalloped inflow edges are shown in some of the later-described embodiments.) The upper (blood outflow) edge is deeply scalloped to leave the three commissure posts 22 and valve leaflets 24 intact, but to cut away porcine aortic root tissue that is not needed between the commissure posts. The reference numbers 26a, 26b, and 26c are applied to the three recesses that result from this scalloping between commissure posts 22. It should be noted, however, that enough tissue is preferably left adjacent to the leaflets so that stitching 60 (FIG. 2) and wire 40 (both described below) can be added without either of elements 40 and 60 being too close to any part of the leaflets in the finished valve. This is believed desirable to avoid any interference with the natural movement of the leaflets, which helps ensure proper closure of the leaflets and avoidance of calcification and tearing.

An annulus of wire 40 is located concentrically outside the blood outflow edge of tissue structure 20. (See also FIGS. 2 and 3.) Wire 40 is shaped to follow the scalloped, blood-outflow edge. Accordingly, wire 40 follows this scalloped edge up to near the apex of each commissure post 22 and down along each recess 26. Wire 40 may be preformed into the appropriate scalloped annular shape as shown in FIG. 3, and then the blood outflow edge of tissue structure 20 may be finally trimmed to closely follow the wire.

It is believed important to match the shape of wire 40 to the tissue structure 20 that it will be used with. Each harvested valve is unique. As just some examples, the lengths of the commissure posts can vary, their spacing around the valve can vary, etc. The wire 40 used in a valve structure should match the particular tissue structure 20 also used in that valve so that the wire supports the tissue structure without distorting its native shape. For example, this means supporting the commissure posts in their native locations, while preferably staying away from any part of the leaflets (as mentioned earlier). To accomplish this, wires 40 may be made available in several different shapes, collectively spanning the range of variations possible in acceptable harvested tissue structures 20. A wire 40 having the shape that best matches a particular tissue structure 20 is then selected as the wire 40 to be used with that tissue structure. (As used in this paragraph, "shape" also includes overall size (diameter) of the valve.)

The functionality of wire 40 is additionally described elsewhere in this specification. Here it will suffice to say that wire 40 is preferably made of a highly resilient (i.e., highly elastically deformable) metal such as nitinol. Wire 40 is preferably strong enough to support commissure posts 22 both radially and annularly. The radial support provided by wire 40 prevents the commissure posts from inadvertently falling inwardly (e.g., over valve leaflets 24) at any time during implantation of the valve into a patient. The annular support provided by wire 40 helps to keep the commissure posts in their proper (native) relative annular positions during implantation of the valve, which can help to ensure that the valve leaflets close properly after the valve has been implanted. On the other hand, wire 40 is preferably not significantly stronger than is sufficient for purposes such as the foregoing. The manner in which wire 40 can be attached to the outside of tissue structure 20 will be considered as part of the following discussion of outer fabric sleeve 50.

The outer surface of tissue structure 20 is preferably completely covered by a sleeve 50 of fabric. Except for the modifications described below that are for the purpose of facilitating the incorporation of wire 40, fabric sleeve 50 and its attachment to tissue structure 20 can be conventional. For example, sleeve 50 can be cut from a tube of knitted or woven dacron or can be of any other suitable material and/or construction.

Figure 2:
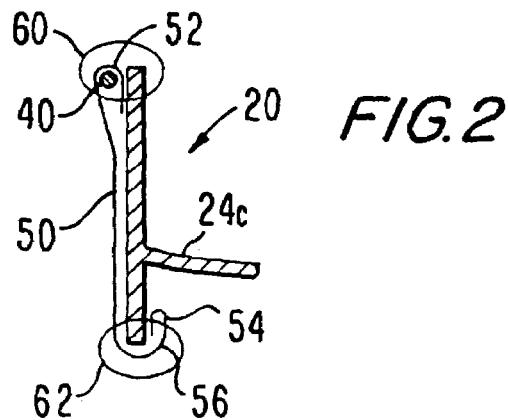
FIG. 2 is a simplified, partial sectional view taken along the line 2-2 in FIG. 1.
Figure 3:
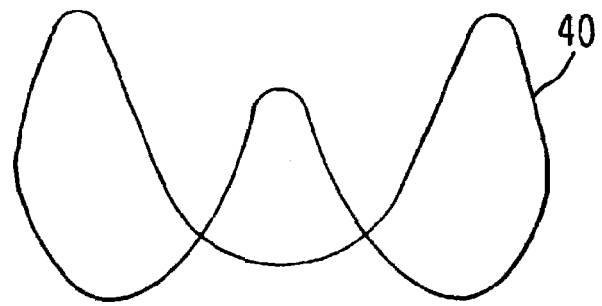
FIG. 3 is a simplified elevational view of one of the components of the heart valve structure shown in FIG. 1.

An upper (blood outflow edge) portion of sleeve 50 can be folded radially inwardly and axially back over wire 40 in the manner of a cuff 52 (see especially FIG. 2). This annular, wire-within-cuff structure can be stitched (e.g., using suture material) to the blood outflow edge of tissue structure 20 all along that edge of the tissue as indicated in a representative way by stitch or suture loop 60. This annular line of stitching secures wire 40 and the blood outflow edge of sleeve 50 to the blood outflow edge of tissue structure 20 annularly all the way around the valve. Thus the same stitching 60 that would conventionally be used to secure together the blood outflow edge of tissue structure 20 and the adjacent edge of fabric sleeve 50 can be used to also secure wire 40 to the other components of the valve structure (because wire 40 follows the blood outflow edges of elements 20 and 50 all the way around the valve structure).

Adjacent the lower (blood inflow) edge of the valve another double cuff of the fabric 50 is formed by folding the extreme end of the fabric radially in and axially back on itself to produce a first cuff 54, and by then folding that first cuff radially in and axially back over and along the blood inflow edge of tissue structure 20 to produce a second cuff 56. This double cuff structure 54/56 is secured to the blood inflow edge of tissue structure 20 by another line of stitching (e.g., of suture material), which extends annularly all the way around the valve as indicated by representative stitch or suture loop 62.

The order in which the two axial ends of sleeve 50 are thus stitched to tissue structure 20 is entirely optional.

Again it is noted that all of elements 40, 60, and 62 are preferably spaced sufficiently far from all parts of leaflets 24 so that, after the valve has been implanted in a patient and is in operation in the patient, there is no interference with the natural movement of the leaflets by any of elements 40, 60, and 62. This is accomplished, at least in part, by making sure that tissue structure 20 includes enough tissue beyond leaflets 24 so that elements 40, 60, and 62 can engage that tissue without coming too close to the leaflets.

Although referred to above as a wire, support structure 40 may alternatively be made in other ways. For example, support structure 40 may be cut from a hollow tube of the appropriate material (e.g., nitinol). If support structure 40 is in fact a wire, ends of the wire may be joined in any of several ways to form a closed annulus. For example, ends of the wire may be welded, brazed, or soldered together, or the ends may be clamped, clipped, or wrapped together by a clamp, clip, or wrapping element.

The valve structure 10 described above is preferably completely fabricated (i.e., manufactured) well in advance of its intended use in a patient. A patient is prepared to receive valve 10 as a replacement for the patient's aortic valve by severing the patient's aorta distal of the patient's natural aortic valve. The patient's natural aortic valve leaflets are removed and valve 10 is substituted. The blood inflow edge of valve 10 is sutured annularly to the patient's heart tissue. Support member 40 helps keep commissure posts 22 from inadvertently folding inwardly during this step, thereby facilitating this part of the implant procedure. Support member 40 can make it possible to omit another complete annular line of sutures around the blood outflow edge of the valve structure. Instead, it can be sufficient to just tack each of commissure posts 22 radially out against the patient's aortic root tissue using suturing through each of the commissure posts.

The radial and annular support of the commissure posts provided by support structure 40 as described above helps to ensure that the commissure posts are tacked at positions that promote proper closure of valve leaflets 24 in the fully implanted and operating valve. There may also be an element of support axial of the commissure posts provided by support structure 40 that is helpful in this regard (i.e., by keeping the commissure posts properly elongated). Between the tacked commissure posts (i.e., in scalloped recesses 26) support member 40 helps to keep the remainder of the blood outflow edge of the valve radially out against the patient's aortic root. This may contribute to the ability of valve 10 to be successfully implanted without the need for a second, complete, annular suture line adjacent the blood outflow edge.

While support structure 40 provides the above-described support for valve 10 especially during implanting, after implanting the significance of support structure 40 diminishes and may eventually become very small or even insignificant. For example, the above-described tacking sutures make continued support of the commissure posts by support structure 40 insignificant. And after the patient's tissue has grown into fabric 50 (as it tends to do over time), support of other portions of the blood outflow edge by support structure 40 also becomes less important.

Data for presently preferred embodiments of support structure 40 and valve structures 10 including such a support structure are as follows: The most preferred material for support structure 40 is nitinol, especially nitinol wire having diameter in the range from about 0.010 in to about 0.018 in. Although nitinol is presently most preferred, other materials such as stainless steel, titanium, and plastics such as urethanes and acetyls (e.g., polyacetyls such as Delrin) are also possible.

To indicate the high degree of flexibility of valve structures 10 constructed with a support structure 40 of nitinol wire having diameter in the nitinol wire diameter range mentioned above, data from various types of deflection tests are provided below. In one type of test the commissure posts 22*a-c* were deflected inward. The radially inward force required to produce a 1 mm inward displacement of a commissure post was found to be approximately 2 g to 10 g. The higher loads mentioned above were required for smaller valve sizes (e.g., 21 mm diameter valves) and thicker nitinol wires (e.g., 0.018 in diameter wires). These data compare with the much higher forces required to produce 1 mm inward deflection of a commissure post in the prior art valves described in Ross et al. U.S. Pat. No. 4,343,048. In particular, the Ross et al. patent reports that in those prior art valves a 50 g to 150 g radially inward force on a commissure post is required to produce a 1 mm inward deflection of the commissure post.

In another type of test, completed valves 10 were functionally tested in a pulse duplicator, simulating the normal blood backpressure (100-120 mmHg) on the valve. The commissure posts 22*a-c* were not anchored (i.e., they were not tacked back as they ordinarily would be in actual use in a patient). The result of this test was that commissure posts 22*a-c* deflected inwardly almost to the center of the valve in response to the normal backpressure produced by the pulse duplicator. For example, for a 25 mm diameter valve, the inward deflection of each commissure post 22*a-c* was approximately 12 mm. This compares to an inward deflection of only about 2 mm for the commissure posts of a conventional, commercially available, 33 mm diameter, stented valve under similar pulse duplicator conditions.

The specifics provided in the three preceding paragraphs are generally characteristics of all embodiments of the present invention, including all of those that will now be described with reference to the other FIGS. 4-22 that form part of this disclosure.

Figure 4:
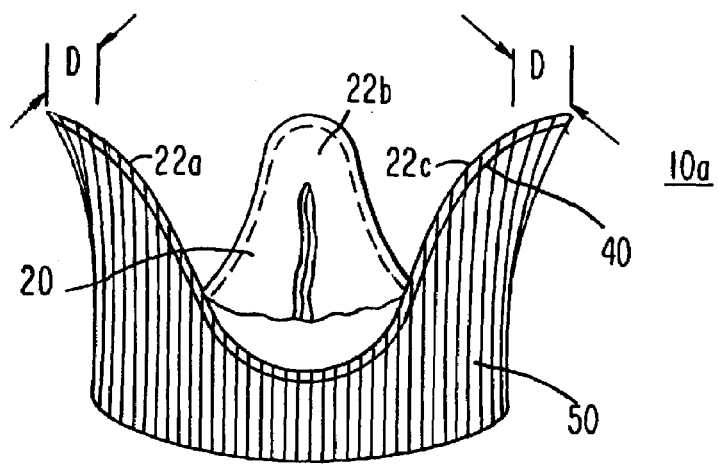
FIG. 4 is a view similar to FIG. 1 showing another illustrative embodiment of the invention.

In the alternative embodiment 10*a* shown in FIG. 4, wire ring (or support structure) 40 is resiliently biased to hold at least commissure posts 22*a-c* radially outwardly (relative to the normally (i.e., native) substantially straight cylindrical shape of tissue structure 20) by a predetermined amount D for each commissure post. When valve structure 10*a* is inserted in a patient, the patient's aortic root tissue radially compresses support structure 40 and the associated parts of valve 10*a* (especially commissure posts 22*a-c*) back to a shape closer to a straight cylinder. However, support structure 40 continues to resiliently urge at least parts of the blood outflow (upper) end of valve structure 10*a* radially outwardly against the patient's aortic root tissue. This can help to hold the valve in place, at least temporarily, during the early stages of the implant procedure. It can also improve the hemostatic behavior of the blood outflow end of valve 10*a* (i.e., between valve 10*a* and the surrounding aortic root tissue) and thereby help reduce the need for a full suture line around the blood outflow end of the valve. It may even reduce the need for tacking sutures through commissure posts 22a-c to the aortic root because the resilient, radially outward, spring bias of support structure 40 continues to urge at least commissure posts 22a-c radially outwardly against the aortic root tissue for as long as valve 10a remains implanted in the patient.

Figure 5:
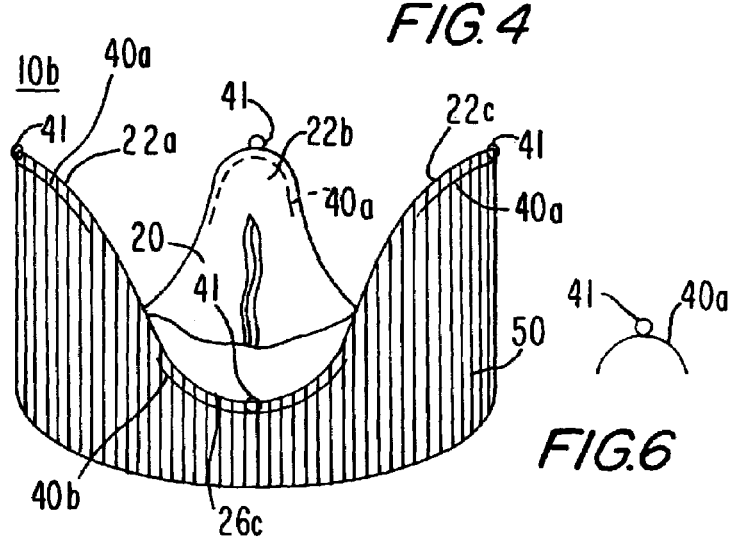
FIG. 5 is another view similar to FIG. 1 showing yet another illustrative embodiment of the invention.

In the still further alternative embodiment 10b shown in FIG. 5 the support structure 40 is made up of several separate segments of types 40a and 40b. In particular, there are three segments of type 40a that alternate with three segments of type 40b annularly around valve structure 10b. To simplify FIG. 5 and to avoid obscuring support structure segments 40a and 40b, fabric sleeve 50 is not shown completely in this FIG. However, it will be understood that this embodiment typically employs a fabric sleeve 50 very much like the fabric sleeves 50 in previously described embodiments.

Each of segments 40a/b is preferably a length of flexible, resilient wire or similar material like that described earlier. Each of segments 40a is shaped to basically follow the blood outflow edge of a respective one of commissure posts 22a-c, but preferably with the addition of a suture loop 41 at about the midpoint of the length of the segment. Each of segments 40b is shaped to basically follow the blood outflow edge of a respective one of recesses 26a-c between the commissure posts, but preferably with the addition of a suture loop 41 at about the midpoint of the length of the segment. Support structure segments 40a and 40b may be secured to the remainder of heart valve structure 10b similarly to the way in which support structure 40 is secured in FIGS. 1 and 2.

Figures 6, 7:
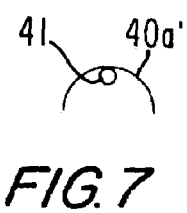
FIGS. 6-9 are simplified elevational views showing illustrative embodiments of certain components of the assembly shown in FIG. 5.
Figures 8, 9:
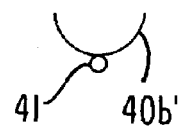

Suture loops 41 are preferably included in segments 40a and 40b to facilitate suturing of the blood outflow end of valve structure 10b inside a patient's aortic root. Tacking sutures can be readily placed through suture loops 41. The remainder of each segment 40a or 40b helps to distribute the force applied by the tacking suture to the adjacent portion of valve structure 10b so that this force is less concentrated in a small area. Suture loops 41 can extend from the associated segment 40a or 40b in either the blood outflow direction (as in FIGS. 5, 6, and 8), or the segments can be made so that suture loops 41 extend from the remainder of the segment in the opposite direction (as in FIGS. 7 and 9). In FIGS. 7 and 9, the alternatively embodied segments are referenced 40a' and 40b', but all further references to segments 40a and 40b herein will be understood to also include the 40a' and 40b', embodiments.

Although segments 40a and 40b are not continuous annularly all the way around valve structure 10b, they are preferably extensive enough to provide some support (of the types described above for structure 40 in other embodiments) for the blood outflow portions of valve structure 10b. Because segments 40a and 40b do not constitute an annularly continuous element, there can be less concern about the possibility of long-term, flexure-fatigue breakage of a support structure made up of such separate segments.

Figure 10:
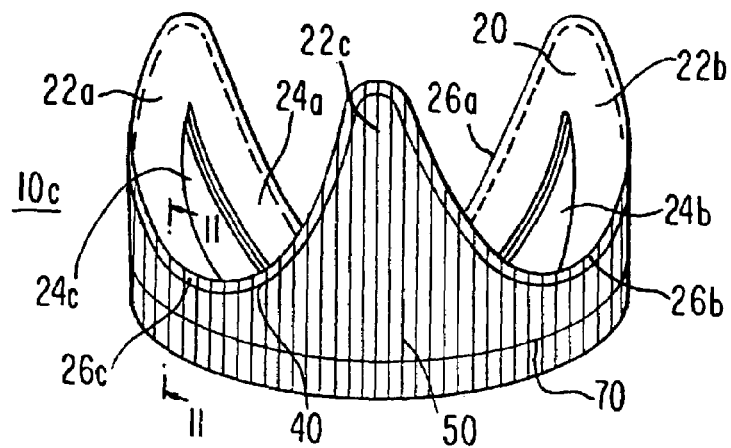
FIG. 10 is another view similar to FIG. 1 showing still another illustrative embodiment of the invention.
Figure 11:
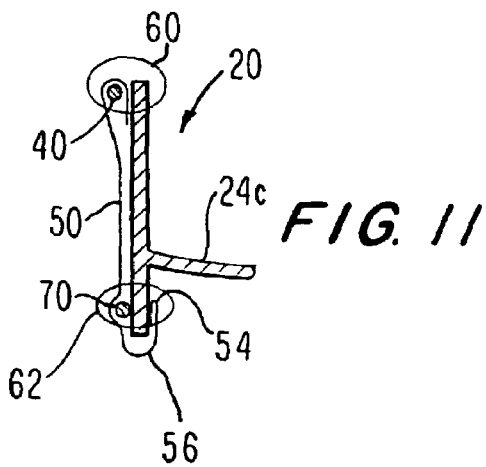
FIG. 11 is a view similar to FIG. 2, but for the embodiment shown in FIG. 10.
Figure 12:
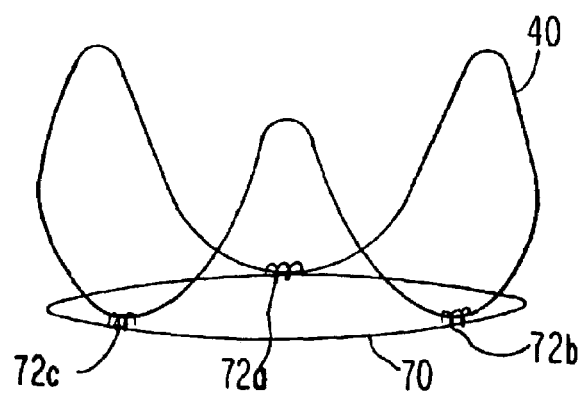
FIG. 12 is a view similar to FIG. 3, but for the embodiment shown in FIG. 10.

FIGS. 10-12 are respectively similar to FIGS. 1-3, but show an alternative embodiment 10c. The features added in FIGS. 10-12 can be included in any of the previously described embodiments as desired. FIGS. 10-12 show the addition of another wire ring 70 near the lower (blood inflow) edge of valve structure 10c. Like wire ring 40, wire ring 70 extends concentrically around tissue structure 20 inside fabric sleeve 50. Wire ring 70 is preferably held in place by annular stitching line 62 (see especially FIG. 11). Wire ring 70 can be completely separate from wire ring 40, or the two can be attached together, such as where they come closest to one another. For example, FIG. 12 shows the two support structures 40 and 70 secured together by three annularly spaced wire wrappings 72a-c, but any other suitable securing technique (such as welding, brazing, soldering, stitching, gluing, crimping a clip, etc.) can be used instead if desired. As another alternative, both of support structures 40 and 70 could be cut as one piece from a tube so that elements 40 and 70 would already be integral with one another. From this example it will again be appreciated that although sometimes described as a wire, support member 70 (like support member 40) does not have to be a wire. The material of support member 70 can be the same as or different from the material of support member 40.

Like support member 40, support member 70 is preferably a relatively light and flexible support. Support member 70 helps to give some additional body or definition to the lower (blood inflow) portion of valve 10c, but it preferably does not greatly alter the overall flexibility of valve 10c. The additional body imparted to the lower portion of valve 10c may help the surgeon make the blood inflow suture ring connection between valve 10c and the patient's heart without inadvertent distortion of the valve as it is sewn in. After the valve has been implanted, however, support structure 70 preferably has little or no effect on the implant.

Figure 13:
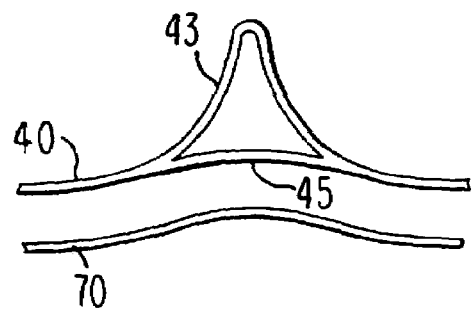
FIG. 13 is a simplified planar projection of a representative portion of exemplary structures that can be used in various embodiments of the invention.

FIG. 13 shows another illustrative embodiment of representative portions of support structures 40 and 70. Although only a portion of each of these support structures is shown in FIG. 13, and although the depicted portions are shown flat, it will be understood that both of structures 40 and 70 are in fact annular (as for the similarly numbered structures in FIGS. 10-12, for example) and include several repetitions (in the annual direction) of what is shown in FIG. 13. FIG. 13 shows that support structure 70 (which can be used like the similarly numbered structure in FIGS. 10-12, for example) can have undulations that are axial of the valve structure as one proceeds annularly around the valve structure. FIG. 13 additionally shows that support structure 40 can be more than a simple, undulating ring. In particular, FIG. 13 shows that adjacent each commissure post 22a-c support structure 40 can have two branches 43 and 45. Branch 43 is shaped to follow the blood outflow edge of the adjacent commissure post 22. Branch 45 runs across the bottom of the adjacent commissure post. The presence of branches 45 may give structure 40 additional stability in the heart valve structure.

As in the case of embodiments like that shown in FIG. 10, structures 40 and 70 in FIG. 13 may be either separate from one another, or they may be linked to one another (e.g., at several locations that are annularly spaced from one another around the heart valve structure).

Figure 14:
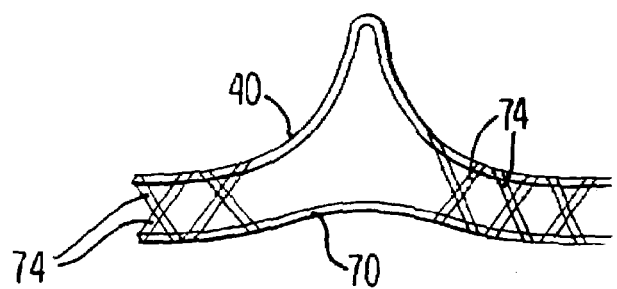
FIG. 14 is another view similar to FIG. 13 for other exemplary structures that can be used in various embodiments of the invention.

FIG. 14 is similar to FIG. 13 for another embodiment having both some similarities to and some differences from the FIG. 13 embodiment. For example, the embodiment in FIG. 14 does not include the branches 45 of support structure 40 that are shown in FIG. 13. However, the embodiment shown in FIG. 14 includes a web or network of links 74 between support structures 40 and 70 at locations that are spaced from one another annularly around the heart valve structure. In the particular example shown in FIG. 14, links 74 are not included in the region of each commissure post 22a-c so as not to reduce the flexibility (especially for radial flexure) of support structure 40 at the commissure posts. Thus in this embodiment links 74 are confined to the regions between the commissure posts.

Links 74 can be included in the embodiment shown in FIG. 14 in any of many different ways. For example, links 74 can be welded, brazed, or soldered to elements 40 and 70.

Or links 74 can be crimped around elements 40 and 70. As yet another example, links 74 can form part of a single unit with elements 40 and 70 (e.g., by cutting all of elements 40, 70, and 74 from a single sheet or tube).

Figure 15:
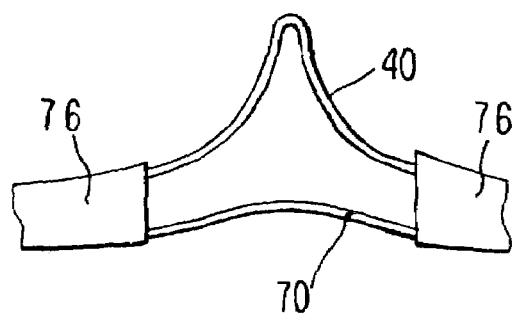
FIG. 15 is yet another view similar to FIG. 13 for still other exemplary structures that can be used in various embodiments of the invention.

FIG. 15 is similar to FIG. 14 for yet another illustrative embodiment. In the FIG. 15 embodiment metal or plastic clips 76 (instead of links 74 as in FIG. 14) are used to provide some connection between support structures 40 and 70. Clips 76 may be configured for crimping onto structures 40 and 70, or there may be an interference fit between clips 76, on the one hand, and structures 40 and 70, on the other hand.

Figure 16:
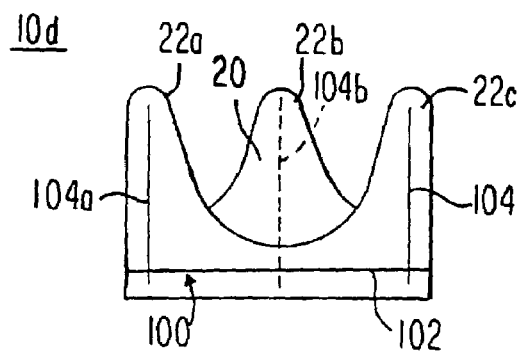
FIG. 16 is a view generally similar to FIG. 1 (although still further simplified) showing yet another illustrative embodiment of the invention.

FIG. 16 shows another alternative embodiment 10d in which support structure 100 includes a flexible annular ring 102 around tissue structure 20 below commissure posts 22a-c. Attached to ring 102 and standing up along each of the commissure posts is a respective one of flexible support fingers 104a-c. Although shown as single members in FIG. 16, it will be understood that support fingers 104a-c could have any of many other shapes. For example, each support member 104 could be an upside-down U or V shape, allowing each member 104 to have two points of attachment to ring 102.

Figure 17:
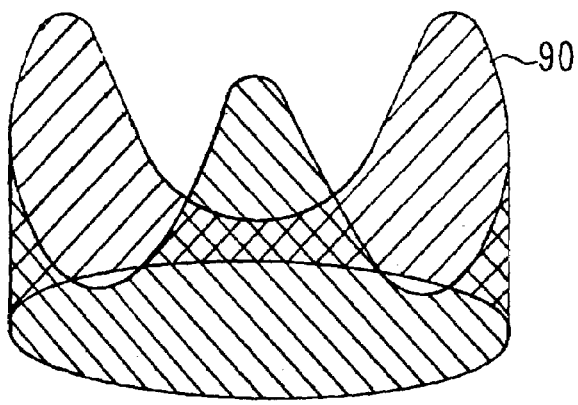
FIG. 17 is a view similar to FIG. 3, but for still another illustrative embodiment of the invention.
Figure 18:
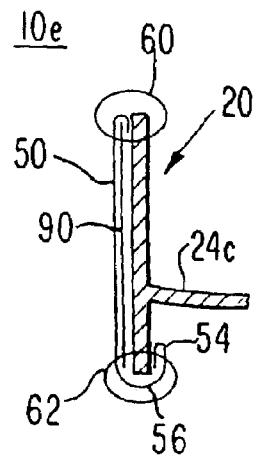
FIG. 18 is a view similar to FIG. 2, but for the embodiment that includes a component like that shown in FIG. 17.

Another alternative embodiment is illustrated by FIGS. 17 and 18. FIG. 17 shows a support structure 90 in the form of a tube or sleeve that is mounted concentrically around the outside of tissue structure 20 but inside fabric sleeve 50 (see also FIG. 18, which is a view similar to FIG. 2 or FIG. 11, but for the alternative embodiment that includes element 90). For clarity in FIG. 17 the portion of sleeve 90 toward the rear is cross-hatched from lower left to upper right, while the portion of that sleeve toward the front is cross-hatched from lower right to upper left. In fact, however, the entire sleeve 90 is typically a perforated or apertured structure or a mesh structure having somewhat more stiffness than tissue structure 20 or fabric sleeve 50. For example, sleeve 90 may be made from a thin sheet or tube of metal or polymer (plastic) that has been laser cut, electroetched, or otherwise processed to convert it to a grid or mesh. Sheet 90 may be secured to the other components of a valve 10e, as shown in representative part in FIG. 18, by annular stitching lines 60 and 62 around the upper (blood outflow) and lower (blood inflow) edges of the valve.

Sheet 90 in valve 10e (FIGS. 17 and 18) acts as a support structure somewhat like previously described support structures 40 and 70, except that sleeve 90 can provide support at substantially all points axially along and annularly around the valve. The degree of support provided by sleeve 90 is similar to that described above for the other illustrative support structures. For example, sleeve 90 provides radial, annular, and axial support for commissure posts 22a-c. It also radially supports the tissue 20 between the commissure posts. And it provides radial support all the way around the lower (blood inflow) edge of the valve. All of these features can facilitate implanting the valve using only one annular suture line adjacent the blood inflow edge, together with tacking sutures for the commissure posts. A second annular suture line adjacent the blood outflow edge may not be needed. All of this suturing can be through sheet 90 (as well as through tissue 20 and fabric 50) to help strengthen the suturing and avoid separation of tissue 20 from any part of the suturing. After the valve has been implanted, the presence of sheet 90 diminishes in importance and may eventually become insignificant.

As in the earlier-described embodiments, the bottom (blood inflow) edge of the valve structure 10e illustrated by FIGS. 17 and 18 can be either straight (e.g., as in FIGS. 1 and 10) or scalloped (e.g., as in FIG. 19, described below). If the bottom edge is scalloped, the scalloping can be of only tissue 20 and fabric sleeve 50, with sheet 90 having a straight bottom edge; or all three components 20, 50, and 90 can have a similarly scalloped bottom edge.

FIG. 19 is similar to FIG. 10 but shows another alternative embodiment 10f in accordance with the invention. In alternative valve 10f the lower (blood inflow) edge of the valve is scalloped. The scalloping shown in FIG. 19 includes axial recesses 82a-c respectively axially opposite commissure posts 22a-c, and axial extensions 86a-c respectively axially opposite recesses 26a-c. Another pattern of scalloping may be used instead if desired. The scalloping may help the blood inflow edge of the valve better match the shape of the site in the patient's heart tissue to which that edge of the valve is to be annularly sutured. Scalloping of the blood inflow edge can be provided in any of the embodiments shown and described herein. Although not shown that way in FIG. 19, support structure 70 could be shaped to follow the scalloped blood inflow edge of the valve.

FIGS. 20 and 21 show an illustrative embodiment of another feature that can be added to any of the valve embodiments shown herein. This additional feature is a sewing or suture cuff or bead 110, which is preferably annular, radially outwardly projecting, and near the blood inflow end or edge of the associated valve 10g. (FIGS. 20 and 21 show a valve structure that is otherwise like the valve structure shown in FIGS. 1-3; but as has been said, a sewing cuff like 110 can be added to any of the other valve structures shown and described throughout this specification.)

Although sewing cuff 110 could alternatively be constructed or provided in other ways, in the illustrative embodiment shown in FIGS. 20 and 21 a ring 112 of soft and flexible material such as a thread or light cord material is provided around tissue structure 20 at the location desired for sewing cuff 110. This ring is covered by conventional fabric sleeve 50, and secured by stitching 62 annularly all the way around the valve structure. The entire sewing cuff structure is preferably relatively easily penetrated by a suture needle. Other examples of suitable fillers 112 for sewing cuff 110 are fabric or textile type materials, a silicone rubber ring, or the like.

Sewing cuff 110 facilitates suturing the adjacent portion of valve structure 10g to the patient's tissue. For example, sutures can be quickly passed through the material 112 of sewing cuff 110 with less need for the greater care required when suturing through tissue structure 20. Sewing cuff 110 also may act somewhat like a gasket to help ensure hemostatic attachment of the adjacent portion of valve structure 10h to the patient's surrounding tissue. By enhancing the hemostatic nature of the blood inflow end or edge suture line, sewing cuff 110 can help reduce the need for a complete second annular suture line adjacent the blood outflow end or edge of any valve structure to which a sewing cuff is added.

Another optional feature that can be employed with the valves of this invention is illustrated by FIG. 22. This feature is a constraint 120 for commissure posts 22a-c. Prior to implanting into the patient, valve structure 10h has a constraint 120 which holds the otherwise free ends of commissure posts 22a-c flexed radially inwardly toward one another. Constraint of the commissure posts in this way may facilitate certain portions of the implant process. For example, this arrangement may facilitate placement of the annular suture line adjacent the blood inflow end or edge of valve structure 10i.

At any desired time during the implant process, constraint 120 may be released and removed. This allows commissure posts 22*a-c* to spring radially out to their final positions against the inside of the patient's aortic root tissue. Support structure 40 promotes this radial outward movement of the commissure posts when constraint 120 is released. Although valve 10*h* is shown with a support structure 40 like that shown, for example, in FIGS. 1-3, it will be understood that constraint feature 120 can be used with any of the valve structures shown and described herein.

Constraint 120 can take any of a wide range of forms. For example, constraint 120 can be a loop of wire, a loop of thread, a loop of suture material, or any other similar structure. As another example, each of commissure posts 22*a-c* could be tied to a constraint ring 120. Each commissure post would then be released by untying or cutting its tie to the ring.

It will be understood that the foregoing is only illustrative of the principles of the invention, and that various modifications can be made by those skilled in the art without departing from the scope and spirit of the invention. As examples of modifications within the scope of the invention, various materials can be used for the support structures (e.g., 40/70/72/74/76/90/etc.) employed in valves in accordance with the invention. Similarly, various materials can be employed for the fabric sleeves 50 employed in these valves, and for the sewing cuff structures 110 that may be optionally included.

The invention claimed is:

1. A replacement heart valve structure for implanting into a patient comprising:
   a tissue structure including an intact heart valve that has been harvested from a mammal and preserved, the tissue structure having an annular blood outflow edge portion that undulates in the axial direction as one proceeds annularly around the annular blood outflow edge portion; and
   a resilient support structure for resiliently supporting the annular blood outflow edge, the resilient support structure comprising an elastically deformable undulating wire ring following the annular blood outflow edge continuously all the way around the tissue structure and being entirely radially outside the outer surface of the tissue structure at the annular blood outflow edge continuously all the way around the annular blood outflow edge, and wherein the undulating wire ring is positioned to surround only the annular outflow edge.

2. The replacement heart valve structure defined in claim 1 wherein the support structure is secured to the annular blood outflow edge.

3. The replacement heart valve structure defined in claim 1 wherein the support structure is made of metal.

4. The replacement heart valve structure defined in claim 3 wherein the metal is selected from the group consisting of nitinol, stainless steel, and titanium.

5. The replacement heart valve structure as defined in claim 1 wherein the support structure comprises an undulating ring of nitinol wire having a diameter in the range from about 0.010 inch to about 0.018 inch.

6. The replacement heart valve structure defined in claim 1 wherein the support structure is made of plastic.

7. The replacement heart valve structure defined in claim 6 wherein the plastic is selected from the group consisting of urethanes and acetyls.

8. The replacement heart valve structure defined in claim 1 wherein the support structure comprises:
   a sleeve that extends annularly around at least an axial portion of the tissue structure.

9. The replacement heart valve structure defined in claim 1 wherein the support structure is configured to resiliently bias at least a portion of the tissue structure radially outwardly.

10. The replacement heart valve structure defined in claim 1 wherein the support structure also has an annular blood inflow edge portion, and wherein the replacement heart valve structure further comprises:
    a second resilient support structure that at least radially supports parts of the tissue structure adjacent the blood inflow edge portion.

11. The replacement heart valve structure defined in claim 1 further comprising:
    a fabric sleeve disposed annularly around the outside of the tissue structure.

12. The replacement heart valve structure defined in claim 11 wherein the support structure is captured between the tissue structure and the fabric sleeve.

13. The replacement heart valve structure defined in claim 1 wherein the tissue structure also has an annular blood inflow edge portion that undulates in the axial direction as one proceeds annularly around the inflow edge portion.

14. The replacement heart valve structure defined in claim 1 further comprising:
    a radially outwardly projecting cuff that extends annularly around the tissue structure for facilitating suturing of the replacement heart valve structure to the patient's tissue.

15. The replacement heart valve structure defined in claim 14 wherein the tissue structure also has an annular blood inflow edge portion, and wherein the cuff is adjacent the blood inflow edge portion.

16. The replacement heart valve structure defined in claim 14 wherein the cuff comprises material that can be penetrated by a suture needle.

17. A replacement heart valve structure for implanting into a patient comprising:
    a tissue structure including an intact heart valve that has been harvested from a mammal and preserved, the tissue structure having an annular blood outflow edge that undulates in the axial direction as one proceeds annularly around the annular blood outflow edge;
    a resilient support structure for resiliently supporting the annular blood outflow edge; the resilient support structure comprising an elastically deformable undulating wire ring following the annular blood outflow edge continuously all the way around the tissue structure and being entirely radially outside the outer surface of the tissue structure at the annular blood outflow edge continuously all the way around the annular blood outflow edge, and wherein the undulating wire ring is positioned to surround only the outflow edge;
    a second resilient support structure that at least radially supports parts of the tissue structure adjacent a blood inflow edge portion, wherein the first and second support structures are connected to one another at a plurality of locations that are annularly spaced from one another around the replacement heart valve structure; and
    a sleeve attached to a portion of the tissue structure and configured to substantially cover the resilient support structures.

18. A replacement heart valve structure for implanting into a patient comprising:
    a tissue structure including an intact heart valve that has been harvested from a mammal and preserved, the tissue structure having an annular blood outflow edge that undulates in the axial direction as one proceeds annularly around the annular blood outflow edge;

a resilient support structure for resiliently supporting the annular blood outflow edge, the resilient support structure comprising an elastically deformable undulating wire ring following the annular blood outflow edge continuously all the way around the tissue structure and being entirely radially outside the outer surface of the tissue structure at the annular blood outflow edge continuously all the way around the annular blood outflow edge, and wherein the undulating wire ring is positioned to surround only the annular outflow edge; and structure for releasably deflecting free end portions of the annular blood outflow edge radially inwardly.

* * * * *